(12) United States Patent
Perring et al.

(10) Patent No.: US 7,781,392 B2
(45) Date of Patent: Aug. 24, 2010

(54) PERFUME COMPOSITIONS

(75) Inventors: Keith Douglas Perring, Kent (GB);
John Martin Behan, Kent (GB);
Jeremy Nicholas Ness, Kent (GB);
Roger John Henry Duprey, Kent (GB);
David Charles Hooper, Kent (GB);
David Anthony McNulty, Kent (GB)

(73) Assignee: Quest International Services B.V., Naarden (NL)

( * ) Notice: Subject to any disclaimer, the term of this patent is extended or adjusted under 35 U.S.C. 154(b) by 374 days.

(21) Appl. No.: 11/578,848

(22) PCT Filed: Apr. 22, 2005

(86) PCT No.: PCT/GB2005/001560
§ 371 (c)(1),
(2), (4) Date: Jun. 21, 2007

(87) PCT Pub. No.: WO2005/103214
PCT Pub. Date: Nov. 3, 2005

(65) Prior Publication Data
US 2007/0287659 A1    Dec. 13, 2007

(30) Foreign Application Priority Data
Apr. 22, 2004   (GB)   .................. 0408962.9

(51) Int. Cl.
*A61K 8/00*   (2006.01)
*A61K 8/18*   (2006.01)
*A61L 9/04*   (2006.01)
*C11D 3/50*   (2006.01)
*A61Q 5/00*   (2006.01)
*A61Q 9/00*   (2006.01)
*A61Q 5/02*   (2006.01)

(52) U.S. Cl. .............................. 512/1; 512/5; 424/70.1; 510/119

(58) Field of Classification Search .................. 512/5, 512/1; 424/70.1; 510/119
See application file for complete search history.

(56) References Cited

U.S. PATENT DOCUMENTS

| 4,522,748 | A | * | 6/1985 | Maurer et al. | .................. 512/17 |
| 5,380,707 | A | * | 1/1995 | Barr et al. | ..................... 512/17 |
| 6,140,295 | A | * | 10/2000 | Behan et al. | ................ 510/320 |

FOREIGN PATENT DOCUMENTS

| EP | 0165458 | * | 12/1985 |
| EP | 0165458 A2 | * | 12/1985 |
| EP | 1 504 744 | | 2/2005 |
| WO | WO 94/16046 | | 7/1994 |
| WO | WO 94/24999 | | 11/1994 |
| WO | WO 98/56337 | | 12/1998 |
| WO | WO 01/16264 | | 3/2001 |
| WO | WO 03/070871 | | 8/2003 |
| WO | WO 2005/044206 | | 5/2005 |

OTHER PUBLICATIONS

Firmenich Product Literature: 922560 "Cetalox TM" and MSDS for "Cetalox TM" 2001, Firmenich item Reference "Cetalox 922560".*
Sawicki Journal of the American Oil Chemists Society vol. 65 No. 6 pp. 1013-1016 1988.*
Cetalox product guide.pdf.*
Cetalox MSDS922560.pdf.*

* cited by examiner

*Primary Examiner*—Milton I Cano
*Assistant Examiner*—Aaron Greso
(74) *Attorney, Agent, or Firm*—Morgan Lewis & Bockius LLP

(57) ABSTRACT

A malodor reducing perfume composition comprising materials a having fruity note and a two groups of an amber note material where the amount of amber and fruity materials together is at least 3% by weight where the total weight percentage of group A amber materials and group B amber materials, WA, is equal to or greater than 0.5% or the total amount of amber and fruity materials together is at least 3+22*(0.5−WA) % by weight where WA is less than 0.5%; wherein amber note materials have an odour threshold lower than that of 1-(2,3,8,8-tetramethyl-1,2,3,4,5,6,7,8octahydronaphthalen-2-yl)ethanone and group B comprises materials with an amber note having an odour threshold equal to or higher than that of 1-(2,3,8,8-tetramethyl1,2,3,4,5,6,7,8-octahydronaphthalen-2-yl)ethanone; the weight ratio of amber note material having to fruity note material in the composition is in the range about 1:30 to 30:1.

3 Claims, No Drawings

PERFUME COMPOSITIONS

This application is filed under 35 U.S.C. 371(c) claiming priority of PCT/GB2005/001560 filed Apr. 22, 2005 which claims priority from GB 0408962.9 filed Apr. 22, 2004, the contents of each application are incorporated herein by reference.

FIELD OF THE INVENTION

This invention relates to perfume compositions. For the purposes of this invention a perfume composition is defined as a mixture of perfume ingredients, if desired mixed with or dissolved in a suitable solvent or solvents and/or mixed with a solid substrate. Perfume ingredients are well known to those skilled in the art, and include those mentioned, for example, in S. Arctander, Perfume and Flavor Chemicals (Montclair, N.J., 1969), in S. Arctander, Perfume and Flavor Materials of Natural Origin (Elizabeth, N.J., 1960) and in "Flavor and Fragrance Materials—1991", Allured Publishing Co. Wheaton, Ill. USA. Perfume ingredients may include natural products such as extracts, essential oils, absolutes, resinoids, resins, concretes etc., and also synthetic basic substances such as hydrocarbons, alcohols, aldehydes, ketones, ethers, acids, esters, acetals, ketals, nitriles, etc., including saturated and unsaturated compounds, aliphatic, carbocyclic and heterocyclic compounds. The invention is particularly concerned with perfume compositions that have the ability to reduce or prevent malodours, i.e. odours generally considered unpleasant or undesirable.

BACKGROUND TO THE INVENTION

Malodours may be encountered in the air and on many substrates such as fabrics, hard surfaces, skin, and hair. Their origin may be personal, from sources such as sweat, urine, and faeces, or environmental, from sources such as gasoline, cooking, and tobacco smoke.

Examples of typical malodourous materials include indole, skatole, and methanethiol found in toilet and animal odours; piperidine and ammonia found in urine; pyridine and trimethylamine found in kitchen and garbage odours; hydrogen sulfide, nicotine, and various pyrroles found in cigarette smoke odours; and short chain fatty acids in axillary malodours.

Prior art approaches used to combat or neutralise malodours include superimposing the malodour with a pleasant stronger odour (i.e. odour masking), cross-adaptation by blocking of the malodour olfactory receptors, suppression of the malodour by mixing with an ingredient that causes a negative deviation of Raoult's law (thereby reducing its partial pressure in air), elimination of the malodour by chemical reaction, absorption of the malodour by a porous or cage-like structure, and avoidance of the formation of malodours by such routes as antimicrobials and enzyme inhibitors. Fragrances may be formulated to be particularly effective in reducing the generation and perception of human body odour. Thus, EP 0545556, U.S. Pat. No. 4,304,679, U.S. Pat. No. 4,906,454, EP 0003172 and EP 0005618 all disclose perfume compositions useful for delivering or enhancing deodorant efficacy, either when applied to human skin directly using a cosmetically acceptable vehicle, or when included in a laundry detergent or fabric treatment product. However, these prior art compositions are not designed to be highly effective on malodours that do not come from bacterial sources, such as cigarette smoke or cooking smoke odours.

Examples of materials have that have been shown to have malodour combating properties include those disclosed by Nogami et al. in WO 98/56337 (amber and musk) and by Schleppnik et al. in U.S. Pat. No. 4,622,221 (cyclohexyl alcohols and ester derivatives), U.S. Pat. No. 4,187,251 (alkyl cyclohexyl alkyl ketones), U.S. Pat. No. 4,310,512 (derivatives of acetic and propionic acids) and U.S. Pat. No. 4,009,253 (4-cyclohexyl-4-methyl-2-pentanone); and by Kulka in U.S. Pat. No. 3,074,891 (esters of alpha-, beta-unsaturated monocarboxylic acids) and U.S. Pat. No. 3,077,457 (fumaric acid esters). These materials, however, are not capable of neutralizing all types of functional groups contained in malodour molecules.

All of the above mentioned documents are hereby incorporated by reference as if recited in full herein.

A distinction is generally made between "masking" and "counteracting" an odour. The term "masking" indicates that a fragrance, usually having a pleasant odour, is introduced. The intensity of the odour from the masking fragrance covers or modifies the objectionable odour or is so intense that it renders the objectionable odour imperceptible. The term "counteracting" indicates that the perceived intensity of the objectionable odour is lower or undetectable in the presence of the counteracting agent. The difference is that a counteracting substance may be used at concentrations that do not overwhelm odour perception and may in fact contribute little or no odour, though it reduces or eliminates the perception of the disagreeable odour. The compositions of this invention may provide both masking and counteracting effects in any given application.

The prior art approaches to malodour reduction remain deficient because they provide only limited options for malodour reduction. Accordingly, there is an ongoing need for additional and improved malodour reducing compositions.

SUMMARY OF THE INVENTION

In one aspect the present invention provides a perfume composition comprising at least 1.0% by weight of one or more materials having a fruity note, and at least 0.5% by weight of at least one material having an amber note, selected from group A or from group B below, wherein the total amount of the material having the amber note and the material having the fruity note in the composition is at least about 3% by weight if no amber material from group B is present, or at least about 25% by weight if no amber material from group A is present, and where materials from both groups A and B are present in amounts above 0.1% w/w the minimum total amount of amber and fruity materials is given by 3% where the total weight percentage of group A materials, $W_A$, is equal to or greater than 0.5%, or by $3+22*(0.5-W_A)$ % where $W_A$ is less than 0.5%; wherein group A comprises materials with an amber note which have a lower odour threshold than 1-(2,3,8,8-tetramethyl-1,2,3,4,5,6,7,8-octahydronaphthalen-2-yl)ethanone and group B comprises materials with an amber note which have an odour threshold that is equal or higher than that of 1-(2,3,8,8-tetramethyl-1,2,3,4,5,6,7,8-octahydronaphthalen-2-yl)ethanone; provided also that the weight ratio of the material having the amber note to the material having the fruity note in the composition is from about 1:30 to about 30:1.

In this specification all percentages are by weight of total composition unless specifically stated otherwise, and all ratios are weight ratios unless specifically stated otherwise.

Perfume compositions in accordance with the invention can have the ability to reduce or prevent malodours or the perception of malodours. The compositions may function by counteracting and/or masking odours.

The invention thus also provides a malodour reducing composition comprising a perfume composition in accordance with the invention.

As used herein, "malodour reducing composition" means a composition which gives the specific impact to a sensory evaluators that malodour on the surface of a substrate or the air in a confined space is reduced after applying such "malodour reducing composition", compared to before such application.

As used herein, "sensory evaluator" is a person having a skill as an expert for physical perfume/odour evaluation, and is screened by odour sensory test and has been trained as a sensory evaluator more than six months.

A fragrance results from a variety of components (materials) in a fragrance composition. Ordinarily, fragrances are created by blending materials (ingredients) comprising odoriferous essential oils, extracts from woods, gums, flowers and other botanicals, resins, animal secretions, and synthetic aromatic materials. These materials are blended in order to achieve what are known as "top note" "middle note" and "bottom note" components. The top note is the refreshing quality sensed upon application. The bottom note is the essence of the fragrance which stays with the wearer for a long time. The middle note is the perceived quality that bridges from top to bottom note.

The fragrance materials themselves are each classified with respect to the aromas (odour) given off, as to providing a green note, amber note, floral note, aldehydic note, fruity note, chypre note, oriental note, leather note, tobacco note, fougere note, etc. Odour descriptions of the majority of the perfume materials listed herein are available in standard texts known within the perfume industry, particularly: "Common Fragrance and Flavor Materials" by Bauer, Garbe and Surburg, VCH Publ., 3$^{rd}$ edition (2001), "Perfume and Flavour Materials", Steffen Arctander (Montclair, N.J., 1969) published in two volumes, "Perfume and Flavor Materials of Natural Origin", S. Arctander (Elizabeth, N.J., 1960).

Preferred compositions of the invention have weight ratios of amber material to fruity material lying in the range 1:30 to 10:1, more preferably in the range of 1:10 to 3:1. The total amount of material having the amber note and the material having the fruity note in particularly preferred compositions is at least about 10% by weight, or more advantageously at least about 30% by weight if no amber material from group B is present, or is at least 30%, or more advantageously 50% if no group A amber material is present. In compositions comprising at least 0.1% by weight of materials from both groups A and B the total amount of material having the amber note and the material having the fruity note in particularly preferred compositions is at least about 20% by weight or more advantageously at least about 30% by weight.

Amber Materials

Materials having an amber note which can be used in the present invention include those selected from the group consisting of natural aromatic chemical materials which are isolated as volatile materials from amber grease, synthetic aromatic chemical materials having aroma similar in nature to the aroma of the natural aromatic chemical materials, derivatives thereof, and mixtures thereof.

Non-limiting examples of these amber materials are as follows, wherein parentheses have the following meaning: [A]=group A amber material; [B]=group B amber material; (Q)=Quest International, (FI)=Firmenich, (G)=Givaudan SA, (H)=Henkel, (IFF)=International Flavors and Fragrances Inc., (K)=Kao. Materials marked with an asterisk are particularly preferred.

1-(2,3,8,8-tetramethyl-1,2,3,4,5,6,7,8-octahydronaphthalen-2-yl)ethanone [B]*, available under various tradenames, e.g. Iso Ambois (Q), Iso E Super (IFF)

2-Methoxyethoxycyclododecane [B]

2-(2,4-dimethylcyclohex-3-en-1-yl)-5-methyl-5-(1-methylpropyl)-1,3-dioxane [A], available under the tradename Karanal (Q)

3a,6,6,9a-tetramethyldodecahydronaphtho[2,1-{b}]furan [A]*available under various tradenames e.g. Amberlyn Super (Q), Cetalox (FI), Ambroxan (H), Ambrox (FI)

1-[2-(1,1-dimethylethyl)cyclohexyloxy]butan-2-ol [B]*

5,5,8,13-tetramethyl-14,16-dioxatetracyclo[11.2.1.0$^{1,10}$.0$^{4,9}$]hexadecane [A]*, having the trivial name Jeger's ketal 3a-Ethyl-6,6,9a-trimethyldodecahydronaphtho[2,1-{b}]furan [A], available under the tradename Grisalva (IFF)

2-(cyclododecyl)-propan-1-ol [B]

Methyl 2,6,10-trimethyl-2,5,9 cyclododecatriene-1-yl ketone [A]*, available under the tradename Cyclisone (Q)

(1-(2,2,6-trimethylcyclohexyl)-3 hexanol) [B]

2,6,6,8-tetramethyl-8-(methyloxy)tricyclo[5.3.1.0$^{1,5}$]undecane [B], having the trivial name methyl cedryl ether and available under the tradename Cedramber (IFF)

1,5,7-trimethyl-13-oxabicyclo[10.1.0]trideca-4,8-diene [A], available under the tradename Cedroxyde (IFF)

{[(ethyloxy)methyl]oxy}cyclododecane [B], available under the tradename Boisambrene (H)

2,4-dimethyl-2-(1,1,4,4-tetramethyltetralin-6-yl)-1,3-dioxolane [A], available under the tradename Okoumal (G).

Materials may be allocated to group A or group B by use of the odour threshold comparison test (OTCT) as set out in Example 2 below.

Fruity Materials

Materials having a fruity note are materials that impart various fruity aroma nuances.

Non-limiting examples of materials having a fruity note are as follows, where parentheses have the same meaning as above, and preferred materials are marked with an asterisk:

Di-isobutyl carbinyl acetate, available under the tradename Alicate (Q)

Allyl Cyclohexyl Propionate

Phenylethyl isoamyl ether, available under the tradename Anther (O)

(2E)-1-(2,2,6-trimethylcyclohex-3-en-1-yl)but-2-en-1-one*, having the trivial name δ-Damascone Dimethyl benzyl carbinyl acetate Ethyl 2,6,6-trimethylcyclohexa-1,3-diene-1-carboxylate*, available under the tradename Ethyl Safranate (Q)

Tricyclo[5.2.1.0$^{2,6}$]dec-4-en-8-yl propanoate*, available under the tradename Florocyclene (Q)

δ-Decalactone

γ-Decalactone 2-(1,1-dimethylethyl)cyclohexyl acetate, available under the tradename Ortholate (Q)

γ-Dodecalactone

δ-Dodecalactone

γ-Undecalactone*

δ-Undecalactone

Ethyl tricyclo[5.2.1.0$^{2,6}$]decane-2-carboxylate, available under the tradename Fruitate (K)

2-Methyldecanenitrile*, available under the tradename Frutonile (Q)

Tricyclo[5.2.1.0$^{2,6}$]dec-4-en-8-yl isobutyrate*, available under the tradename Gardocyclene (Q)

Tricyclo[5.2.1.0$^{2,6}$]dec-4-en-8-yl acetate*, available under the tradename Jasmacyclene (Q)

2-Ethyl-N-methyl-N-(3-methylphenyl)butanamide*

2-Hexylcyclopentanone, available under the tradename Jasmatone (Q)

2,4,4,7-Trimethyl-6,8-nonadienone oxime, available under the tradename Labienone Oxime (G)

2-[2-(4-methylcyclohex-3-en-1-yl)propyl]cyclopentanone, available under the tradename Nectaryl (G).

2,7-dimethyl-1,0-(1-methylethyl)-1-oxaspiro[4,5]deca-3,6-diene* tricyclo[5.2.1.0$^{2,6}$]dec-3-en-8-yl 2,2-dimethylpropanoate*, available under the tradename Pivacyclene (Q).

While specific ingredients are set forth in the foregoing as providing the amber and fruity notes, the present invention is not limited to these specific ingredients. Other intense, powerful ingredients providing amber and fruity notes can be used instead or additionally.

While essential components of the present invention include materials providing amber and fruity notes, the composition of the invention may additionally include other materials providing other notes.

The compositions of this invention may also include diluents and/or solvents, such as (but not limited to) water; C1-C4 monohydric alcohols; C2-C6 polyhydric alcohols; propylene carbonate; liquid polyalkylene glycols; triethyl citrate; isopropyl myristate; benzyl benzoate, diethyl phthalate, dipropylene glycol, etc. These materials are used for, e.g., solubilizing or diluting some solid or viscous ingredients in the compositions of the present invention to, e.g., improve handling and/or formulating, or stabilizing volatile ingredients, e.g., by reducing their vapor pressure.

Preferred perfume compositions comprise at least two materials having a fruity note. Particularly preferred compositions comprise at least 8% by weight of amber material, more particularly one or more group B amber materials, together with at least 10% of at least two materials having a fruity note. The following fruity materials may be used to advantage in such compositions: Jasmacyclene, ethyl safranate, Alicate, Jasmatone, 2-ethyl-N-methyl-N-(3-methylphenyl)butanamide, Florocyclene and allyl cyclohexyl propionate. The following group B amber materials are also of particular utility: Iso Ambois, 2-methoxyethoxycyclododecane, and 1-[2-(1,1-dimethylethyl)cyclohexyloxy]butan-2-ol.

Perfume compositions in accordance with the invention have been found to be particularly effective in reducing or preventing axillary malodour (i.e. under-arm odour) and so find particular application in consumer products such as fabric-care products e.g. fabric detergents, fabric conditioners and fabric fresheners and skin-care products e.g. deodorants, antiperspirants, soaps, etc. The compositions are also useful in relation to other malodours and find application in other consumer products.

The invention also includes within its scope a consumer product comprising a composition in accordance with the invention.

The present invention also relates in a further aspect to a consumer product comprising at least one material having an amber note and at least one material having a fruity note, wherein the total amount of the material having an amber note and the material having a fruity note in the product is from about 0.001% to about 5% by weight.

Non-limiting examples of consumer products which can be applied to the present invention include: fabric freshening compositions; fabric detergents and conditioners, household cleaning compositions; hair treating compositions; antiperspirants; deodorants; and air freshening compositions; wherein the consumer products containing an effective amount of the malodour reducing composition.

The amount of the composition having at least one material having an amber note and at least one material having a fruity note in the consumer product of the present invention is from about 0.001% to about 5% by weight, preferably, from about 0.005% to about 2%, more preferably, from about 0.01% to about 1.0%.

The compositions of this invention can be capable of effectively reducing malodours when utilized in small quantities and in many different mediums. For instance, use in room fresheners or room deodorants in the form of aerosols (sprays, etc.), liquids (wick type), solids (wax bases as in pomander, plastics, etc.), powders (sachets, dry sprays) and gels (solid gel sticks) are particularly preferred. Other illustrative uses are in clothes deodorants as applied by washing machine applications such as in detergents, powders, liquids, whiteners or fabric softeners or by other applications such as closet blocks, closet aerosol sprays, or clothes storage areas or in dry cleaning to overcome residual solvent notes on clothes; in bathroom accessories such as paper towels, bathroom tissues, sanitary napkins, towellets, disposable wash cloths, disposable diapers, and diaper pail deodorants; in cleansers such as disinfectants and toilet bowl cleaners; in cosmetic products such as antiperspirant and underarm deodorants, general body deodorants in the form of powders, aerosols, liquids or solid, or hair care products such as hair sprays, conditioners, rinses, hair colors and dyes, permanent waves, depilatories, hair straighteners, hair groom applications such as pomade; creams, lotions, etc., medicated hair care products containing such ingredients as S-Selenium-sulfide, coal tar, salicylates, etc., or shampoos, or foot care products such as foot powders, liquids or colognes, after shaves and body lotions, or soaps and synthetic detergents such as bars, liquids, foams or powders; in odour control such as during manufacturing processes, such as in the textile finishing industry and the printing industry (inks and paper); in effluent control such as in processes involved in pulping, stock yard and meat processing, sewage treatment, or garbage disposal, or in product odour control as in textile finished goods, rubber finished goods, car fresheners, etc.; in agricultural and pet care products such as dog and hen house effluents, and domestic animal and pet care products such as deodorants, shampoo or cleaning agents, or animal litter materials; in large scale closed air systems such as auditoriums, and subways and transport systems.

The following specific consumer products further describe the preferred examples within the scope of present invention.

(i) Fabric Freshening Compositions

The fabric freshening composition of the present invention preferably includes: from about 0.001% to about 1% of a perfume composition of the present invention; optionally with from about 0.01% to about 5% of a malodour reducer such as an odour-complexing salt or a cyclodextrin; and the balance comprising carrier.

(ii) Household Cleaning Composition

The household cleaning compositions of the present invention encompass both laundry and surface cleaners and generally include: from about 0.001% to about 2% of a perfume composition of the present invention; from about 0.01% to about 60% of a surfactant; one or more adjunct ingredients selected from the group consisting of abrasives, builders, bleaches, bleach boosters, bleach activators, clays, thickeners, dispersants, enzymes, dyes, colorants, filler salts, hydrotropes, enzymes, preservatives, anti-oxidants, chelants, stabilizers, germicides, fungicides, solvents, photodisinfectants, and mixtures thereof; and the balance comprising carrier.

(iii) Hair Treating Composition

The hair treating composition of the present invention generally includes: from about 0.001% to about 2% of a perfume composition of the present invention; from about 0.01% to about 10% of a fixative polymer; and the balance comprising water. Non-limited Preferable examples of hair treating compositions of the present invention include: mousse, hair spray, hair mist, gel, and hair tonic.

(iv) Antiperspirant and/or Deodorant Compositions

The antiperspirant and/or deodorant compositions of the present invention generally includes: from about 0.001% to about 2% of a perfume composition of the present invention, in addition to carrier fluids, emollients, deodorant actives, optional adjuncts and, in the case of antiperspirants, between 0.5% and around 40% of antiperspirant. Full disclosures on suitable formulations are given in 'Antiperspirants and Deodorants', K Laden (editor), Dekker (1999).

(v) Air Freshening Compositions

The air freshening composition of the present invention generally includes: from about 0.01% to about 5% of a perfume composition of the present invention; and from about 0.01% to about 95% of one or more volatile solvents, in addition to optional adjuncts such as dyes, stabilizers, etc.

The consumer products of the present invention are used in conventional ways to provide the desired benefit appropriate to the product such as freshening fabrics, freshening air, freshening and styling hair, freshening and holding hair, freshening and cleaning household products, the like. Such methods of use depend upon the type of composition employed but generally involve application of an effective amount of the product to the fabrics, households, hair or skin, which can then be allowed to remain on the surface of fabrics/ households, (as in the case of fabric freshening compositions/ household cleaning compositions; allowed to remain on the hair (as in the case of spray, mousse, or gel products); or allowed to remain on the skin (as in the case of the antiperspirants/deodorants). By "effective amount" is meant an amount sufficient to provide the benefit desired.

The aspects and embodiments of the present invention set forth in this document have many surprising advantages, including providing malodour reducing compositions which provide malodour impression on surfaces of, e.g., skin, tiles, fabrics and hair, that are contaminated with environmental odours such as cigarette smoke odours, cooking smoke odours and/or that are wetted with perspiration, air in confined spaces such as bathrooms and kitchens and in consumer products which contain materials which are inherently malodourous, with substantially no odour or faint odour impression on the surfaces after treating the compositions.

The consumer products according to the present invention may be produced by the same processing steps as used for prior consumer products, with the perfume composition according to the present invention being substituted for previous, conventional fragrance compositions. It is generally preferable for the perfume composition to be added near the end of the consumer product manufacture, in order to avoid volatilization of components, particularly where heating is utilized in forming the consumer product (for example, in melting solid ingredients of the vehicle in forming a stick deodorant). The compositions of the present invention may be advantageously used in conjunction with the prior art fragrance technologies described above.

The invention also provides a method of reducing or preventing a malodour, comprising applying a perfume composition or consumer product in accordance with the invention to a substrate or airspace.

The invention also covers use of a perfume composition or consumer product in accordance with the invention for the purpose of reducing or preventing a malodour.

In a further aspect the invention provides a method of testing a composition for efficacy in reducing malodour on fabric following washing in a detergent system, comprising washing test fabric in a detergent system including a composition under test, assessing reduction in malodour, and comparing the results with those obtained by washing in a control detergent system without a composition under test, wherein the washing is performed in the presence of additional soil and using less than the recommended dose of the detergent system.

The method of testing of the invention uses more demanding conditions than is conventional and is found to provide a more sensitive test that yields greater differences between compositions under test, thus enabling identification of compositions useful in demanding situations.

The additional soil conveniently comprises a standard soil, e.g. a sheet of wfk SBL from WFK Testgewebe GmbH.

The detergent system is desirably used at half the recommended dose, e.g. 55 g instead of 110 g.

The detergent system may comprise a laundry powder or laundry liquid, and is preferably unperfumed (apart from the composition under test).

The reduction in malodour is preferably assessed by trained sensory evaluators.

The fabric desirably has a standard malodour, e.g. axillary malodour on test cloths worn by suitably selected panellists.

The invention will be further described, by way of illustration, in the following Examples.

EXAMPLES

Example 1

Laundry Malodour Reduction Test (LMRT)

This test uses trained sensory evaluators to assess the reduction in perceived malodour following washing in a detergent system of test fabric samples that have been worn by panellists, inserted in the underarm region of shirts supplied to them. The test may be applied in two different modes, depending upon the wash system chosen. In the conventional 'Clean System' mode, the wash process comprises a standard wash of test fabric samples worn by panellists for a working day prior to laundry treatment with a commercially available unperfumed laundry powder, as detailed in the protocols set out below. In the 'Soiled System' mode used in the present application, the wash comprises in addition a standard soil provided by a commercially available soil strip (wfk SBL as discussed below), and utilises a lower concentration of the laundry powder (55 g instead of 110 g per machine load). Except for these differences, all the protocols of the 'Soiled System' are identical to those of the 'Clean System' wash. In both cases, the laundry powder may contain a perfume composition under test, to determine the effect on malodour reduction compared with unperfumed controls.

Panel Selection

A panel consists of about 50 subjects who have been selected by expert odour assessors for baseline under-arm odour that is not unusually weak or uneven between the axillae. Subjects are required to adhere to a number of restrictions in order to standardize their under-arm odour production; they should avoid eating spicy, highly flavoured foods, such as curry and garlic, and they should not go swimming during the test. Panellists are also requested to avoid wearing perfume and perfumed cosmetics, including aftershave when they attend for the test.

Panellists are denied the use of their own under-arm product at all times. All panellists are routinely screened at the start of each week's test to ensure that they have not been using antiperspirants. Panellists are not permitted to wash their under-arm areas during a test. They are supplied with a non-deodorant soap bar for home use, and a placebo alcoholic deodorant aerosol and aftershave for use between tests, at weekends and during holidays. A note of guidance is issued to new panellists. New panellists are put on a placebo treatment for at least 2 weeks to screen their baseline under-arm odour level. Subjects who suffer from skin disorders, show evidence of sensitive skin or are receiving medication are excluded from the panel.

Washing of the Panellists

Prior to the panellists putting on the shirts supplied, the assessors used unperfumed soap to wash the axillae. A standard washing technique is used in which a wet flannel is soaped, typically for 10 seconds, the axillae washed with the flannel, typically for 15 seconds, then wiped with a water-rinsed flannel and dried with a paper towel. A separate flannel is used for each axilla of each panellist. Flannels are washed at 95° C. with a pinch of powder and dried thoroughly.

Test Procedure—Fabric Preparation, Laundering Operations, etc.

During the test, panellists are supplied with shirts as an integral part of the fabric product deodorancy test. They are assigned polycotton shirts to wear that have been washed in an unperfumed regular European laundry powder comprising around 10% anionic surfactant (eg sodium alkylbenzenesulphonate), sodium carbonate 20-30% and 5-10% peroxide (eg sodium percarbonate) plus optional adjuncts such as small quantities of non-ionic surfactants, chelators, peroxide activators, enzymes and dyes.

The shirts are prepared by being washed at 40° C. with a measured amount of the unperfumed laundry powder using European washing machines, 10 shirts per washing machine and 5 per tumble drier. Test fabric samples comprise 100% cotton sheet fabric pieces each approximately of size 35 cm×25 cm, and weight 12.5 g which are selected as test cloths of a balanced incomplete randomization design. All of the fabric pieces are pre-washed in the laundry powder, dried and then labelled to indicate the intended test treatment. The test fabric samples are inserted into the shirts (using double sided tape) in the underarm regions, ready for wear by the panellists the next working day.

The shirts, including the inserted test fabric samples, are worn by the panellists for a working day. The fabric samples are then removed and treated by washing using the 'Soiled System' as discussed above, i.e. with added soil and a reduced dose (55 g) of laundry powder under test. Laundry powders under test comprise the unperfumed laundry powder as discussed above including a perfume composition to be tested, typically at a concentration of 0.3% by weight, mixed in a conventional manner. Typically up to 5 different laundry powders, each including a different perfume composition, are tested at the same time, depending on the number of panel lists.

Test operators perform all laundering operations of the test fabric samples using European washing machines at 40° C. followed by line drying of the test fabric samples for approx 2 hrs. Each wash consists of at least 20 test fabric samples and made up to a wash load of 1 kg with additional cotton fabric. In the Soiled System test one soiled cloth, as discussed below, is also included in the wash load for each product under test. The soiled cloth is a sheet of 'wfk SBL', a cotton soil ballast fabric that contains 8 grams of soil and is manufactured by the company WFK Testgewebe GmbH. The soiled cloths are kept refrigerated until required for use.

The contents of the soil ballast on the wfk SBL fabric are as follows: —

20% Protein (from egg white powder)

15% Starch (corn starch)

15% Kaoline

15% Salt (NaCl)

10% Vegetable oil (Olio Extra Vergine di Oliva)

6% Emulgator (Uniperol Dispersing agent, BASF)

5% Pigment Carpet Soil 'wfk 09W' (made up of 55% Kaolin, 43% Quartz, 1.5%

Soot, 0.5% Eisenoxid Schwarz

5% Mineral Oil

5% Urea (synthetic)

4% Calcium chloride

Evaluation

After the used test fabric samples have been washed and dried, they are folded and placed into coded bags for a period of 40 mins. The samples are then assessed by the trained sensory evaluaters. Each trained assessor (minimum of three and desirably five or more) assigns a score on the scale zero to 2 for odour intensity. Assessors operate without knowledge of the products used or of the results of the evaluations of their fellow assessors. Assessors record their scores, conveniently on a handheld computer such as a Palm V.

Statistical Analysis

The data from the panels are analysed using multivariate analysis, for example using the suite of software provided by the SAS Institute. Differences between treatments are evaluated using a protected t-test. The data is initially presented as LMRT malodour scores and in turn this may be 'converted' into % malodour reduction in relation to the unperfumed powder score.

Extensive testing of perfume compositions was carried out using the above protocol, and LMRT malodour scores were determined using the 'Soiled System'. The tests revealed surprisingly effective formulation patterns. Examples of these are given below. In these tests, unperfumed controls had LMRT malodour scores between about 1.8 and 2.0, and perfumes of the prior art tended to yield LMRT malodour scores of about 0.8 to 1.4. The exemplified perfume compositions in accordance with the invention have LMRT malodour scores of less than 0.8.

Equivalent tests carried out in the 'Clean System' mode yielded much lower levels of difference between perfume compositions under test, reducing the ability to identify compositions useful in more demanding situations.

Example 2

Odour Threshold Comparison Test (OTCT)

The object of the test is to determine whether the odour threshold of a test material is higher, lower, or equal to that of a standard amber material, 1-(2,3,8,8-tetramethyl-1,2,3,4,5, 6,7,8-octahydronaphthalen-2-yl)ethanone. A range of serial dilutions of each compound is prepared in parallel, starting from a low concentration at which the standard amber is not detectable. The dilutions must be made using an appropriate diluent that is, one that is chemically compatible, safe for use in this test, and with no odour or very low odour. A material such as diethyl phthalate (DEP) is suitable.

Typically, two sets of nine concentrations of each compound were prepared in jars. These series were arranged in two rows, ascending by concentration. Panellists established at which point one material became detectable by sniffing the headspace. The amber material was classified on the basis of being a group A material if it was the first material to be detected by over 50% of a panel of assessors, else it would be classified as belonging to group B. If no detectable odour is discovered, the test is repeated starting from a higher concentration.

Example 3

Onwards

The following Examples of malodour reducing compositions further describe and demonstrate embodiments within the scope of the present invention. These Examples are given solely for the purpose of illustration and are not to be construed as limitations of the invention.

Amounts are in percent by weight, of the total weight of the composition. The diluent used in every case was dipropylene glycol.

Parentheses have the following meaning: (A)=Group A amber material; (B)=Group B amber material; (F)=fruity material; (Q)=Quest International, (FI)=Firmenich, (G)=Givaudan SA, (H)=Henkel, (IFF)=International Flavors and Fragrances Inc., (K)=Kao.

Example 4

| | |
|---|---|
| BANGALOL(Q) | 8.33 |
| BOURGEONAL(Q) | 8.33 |
| DAMASCONE DELTA | 1.67(F) |
| EUGENOL | 8.33 |
| ISO AMBOIS(Q) | 16.67(B) |
| NECTARYL(G) | 8.33(F) |
| DILUENT | 48.33 |

LMRT score = 0.33

Example 5

| | |
|---|---|
| BOURGEONAL(Q) | 8.33 |
| CETALOX(FI) | 1.67(A) |
| GERANYL NITRILE | 8.33 |
| INTERLEVEN ALDEHYDE | 1.67 |
| LILY ALDEHYDE | 16.67 |
| 2,7-DIMETHYL-10-(1-METHYLETHYL)-1-OXASPIRO[4.5]DECA-3,6-DIENE | 1.67(F) |
| DILUENT | 61.67 |

LMRT score = 0.15

Example 6

| | |
|---|---|
| METHYL IONONE, ALPHA ISO | 16.67 |
| ALICATE(Q) | 16.67(F) |
| 1-[2-(1,1-DIMETHYLETHYL)CYCLOHEXYLOXY]BUTAN-2-OL | 16.67(B) |
| CETALOX(FI) | 1.67(A) |
| FRUITATE | 1.67(F) |
| KARANAL | 1.67(A) |
| DILUENT | 45 |

LMRT score = 0.30

Example 7

| | |
|---|---|
| ETHYL SAFRANATE(Q) | 1.67(F) |
| GYRANE(Q) | 8.33 |
| ISO AMBOIS(Q) | 16.67(B) |
| JASMACYCLENE(Q) | 16.67(F) |
| LILIAL(G) | 16.67 |
| MUSK R1(Q) | 1.67 |
| DILUENT | 38.33 |

LMRT score = 0.25

Example 8

| | |
|---|---|
| METHYL IONONE, ALPHA ISO | 16.67 |
| ALDEHYDE MNA | 1.67 |
| CYCLISONE(Q) | 16.67(A) |
| ISO AMBOIS(Q) | 16.67(B) |
| LABIENONE OXIME(G) | 1.67(F) |
| SILVANONE M | 16.67 |
| DILUENT | 30 |

LMRT score = 0.57

Example 9

| | |
|---|---|
| 2-METHOXYETHOXYCYCLODODECANE | 8.33(B) |
| CYCLOPENTADECANOLIDE | 8.33 |
| DAMASCONE DELTA | 1.67(F) |
| FLOROCYCLENE(Q) | 16.67(F) |
| RHUBAFURAN | 1.67 |
| TRIDECENENITRILE | 1.67 |
| DILUENT | 61.67 |

LMRT score = 0.42

Example 10

| | |
|---|---|
| CETALOX FI) | 1.67(A) |
| EUGENOL | 8.33 |
| FRUTONILE(Q) | 8.33(F) |
| JASMACYCLENE(Q) | 16.67(F) |
| LABIENONE OXIME(G) | 1.67(F) |
| METHYL DIHYDROJASMONATE | 16.67 |
| DILUENT | 46.67 |

LMRT score = 0.48

Example 11

| | |
|---|---|
| BANGALOL(Q) | 8.33 |
| CYCLISONE(Q) | 16.67(A) |
| DYNASCONE(FI) | 1.67 |
| INTRELEVEN ALDEHYDE | 1.67 |
| JASMATONE(Q) | 8.33(F) |
| METHYL DIHYDROJASMONATE | 16.67 |
| DILUENT | 46.67 |

LMRT score = 0.45

Example 12

| | |
|---|---|
| METHYL IONONE, ALPHA ISO | 16.67 |
| ALLYL CYCLOHEXYL PROPIONATE | 16.67(F) |
| BENZYL SALICYLATE | 16.67 |
| CETALOX(FI) | 1.67(A) |
| ETHYLENE BRASSYLATE | 8.33 |
| EUGENOL | 8.33 |
| DILUENT | 31.67 |

LMRT score = 0.66

Example 13

| | |
|---|---|
| ANTHER(Q) | 8.33(F) |
| 5,5,8,13-TETRAMETHYL-14,16-DIOXATETRACYCLO[11.2.1.0$^{1,10}$.0$^{4,9}$]HEXADECANE | 1.67(A) |
| CETALOX(FI) | 1.67(A) |
| DAMASCONE DELTA | 1.67(F) |
| PHENYLETHYL PHENYLACETATE | 16.67 |
| SILVANONE M | 16.67 |
| DILUENT | 53.33 |

LMRT score = 0.53

Example 14

| | |
|---|---|
| ALLYL CYCLOHEXYL PROPIONATE | 16.67(F) |
| BOURGEONAL(Q) | 8.33 |
| CYCLISONE(Q) | 16.67(A) |
| IONONE BETA | 8.33 |
| JASMACYCLENE(Q) | 16.67(F) |
| YARA | 8.33 |
| DILUENT | 25 |

LMRT score = 0.45

Example 15

| | |
|---|---|
| CETALOX(FI) | 1.67(A) |
| ELINTAAL(Q) | 8.33 |
| FLOROCYCLENE(Q) | 16.67(F) |
| ISO AMBOIS(Q) | 16.67(B) |
| JADENOL(Q) | 8.33 |
| JASMATONE(Q) | 8.33(F) |
| DILUENT | 40 |

LMRT score = 0.36

Example 16

| | |
|---|---|
| 1-[2-(1,1-DIMETHYLETHYL)CYCLOHEXYLOXY]BUTAN-2-OL | 16.67(B) |
| 2-METHOXYETHOXYCYCLODODECANE | 8.33(B) |
| BENZYL SALICYLATE | 16.67 |
| ISO AMBOIS | 16.67(B) |
| 2-ETHYL-N-METHYL-N-(3-METHYLPHENYL)BUTANAMIDE | 8.33(F) |
| SILVANONE M | 16.67 |
| DILUENT | 16.67 |

LMRT score = 0.63

Example 17

| | |
|---|---|
| BOURGEONAL(Q) | 8.33 |
| COUMARIN | 8.33 |
| CYPRISATE(Q) | 8.33 |
| DAMASCONE DELTA | 1.67(F) |
| ISO AMBOIS(Q) | 16.67(B) |
| KARANAL(Q) | 1.67(A) |
| DILUENT | 55 |

LMRT score = 0.55

Example 18

| | |
|---|---|
| 5,5,8,13-TETRAMETHYL-14,16-DIOXATETRACYCLO[11.2.1.0$^{1,10}$.0$^{4,9}$]HEXADECANE | 1.67(A) |
| ETHYL SAFRANATE(Q) | 1.67(F) |
| EUGENOL | 8.33 |
| MUSK MC4 | 16.67 |
| NECTARYL(G) | 8.33(F) |
| YARA | 8.33 |
| DILUENT | 55 |

LMRT score = 0.79

Example 19

| | |
|---|---|
| AMYL SALICYLATE | 16.67 |
| CETALOX(FI) | 1.67(A) |
| CYPRISATE(Q) | 8.33 |
| ETHYL SAFRANATE(Q) | 1.67(F) |
| 2-ETHYL-N-METHYL-N-(3-METHYLPHENYL)BUTANAMIDE | 8.33(F) |
| ROSSITOL(Q) | 8.33 |
| DILUENT | 55 |

LMRT score = 0.39

Example 20

| | |
|---|---|
| ALICATE(Q) | 16.67(F) |
| AQUANAL(Q) | 8.33 |
| BICYCLONONALACTONE | 1.67 |
| ISO AMBOIS(Q) | 16.67(B) |
| MOSS OAKMOSS SYNTHETIC | 1.67 |
| RHUBAFURAN(Q) | 1.67 |
| DILUENT | 53.33 |

LMRT score = 0.53

Example 21

| | |
|---|---|
| 2-METHOXYETHOXYCYCLODODECANE | 8.33(B) |
| AMYL SALICYLATE | 16.67 |
| CETALOX(FI) | 1.67(A) |
| COUMARIN | 8.33 |
| HABANOLIDE(FI) | 16.67 |
| PIVACYCLENE(Q) | 8.33(F) |
| DILUENT | 40 |

LMRT score = 0.47

The invention claimed is:

1. A perfume composition, comprising at least 1.0% by weight of one or more materials having a fruity note; and at least 0.5% by weight of at least one material having an amber note selected from at least one of group A and group B below, wherein the total amount of material having an amber note and material having a fruity note in the composition is
   (a) at least about 3% by weight if no amber material from group B is present, or
   (b) at least about 25% by weight if no amber material from group A is present, or
   (c) where materials from both groups A and B are each present in an amount of at least 0.1% w/w, the total amount of amber and fruity materials together is at least 3% by weight where the total weight percentage of group A materials, $W_A$, is equal to or greater than 0.5% or the total amount of amber and fruity materials together is at least 3+22'(0.5-$W_A$) % by weight when $W_A$ is less than 0.5%;

wherein group A comprises materials with an amber note having an odour threshold lower than that of 1-(2,3,8,8-tetramethyl-1,2,3,4,5,6,7,8-octahydronaphthalen-2-yl) ethanone and group B comprises materials with an amber note having an odour threshold equal to or higher than that of 1-(2,3,8,8-tetramethyi-1,2,3,4,5,6,7,8-octahydronaphthalen-2-yl)ethanone; provided also that the weight ratio of material having an amber note to material having a fruity note in the composition is in the range about 1:30 to 30:1, and wherein said at least one fragrance material having an amber note is selected from the group consisting of:

1-(2,3,8,8-tetramethyl-1,2,3,4,5,6,7,8-octahydronaphthalen-2-yl)ethanone,
2-methoxyethoxycyclododecane,
2-(2,4-dimethylcyclohex-3-en-1-yl)-5-methyl-5-(1-methyipropyl)-1,3-dioxane,
3a,6,6,9a-tetramethyldodecahydronaphtho[2,1-{b}]furan,
1-[2-(1,1-dimethylethyl)cyclohexyloxy]butan-2-ol,
5,5,8,13-tetramethyl-14,16-dioxatetracyclo [11.2.1.0$^{1,10}$.0$^{4,9}$]hexadecane,
3a-ethyl-6,6,9a-trimethyldodecahydronaphtho[2,1-{b}]furan,
2-(cyclododecyl)-propan-1-ol,
methyl 2,6,10-trimethyl-2,5,9 cyclododecatriene-1-yl ketone,
(1-(2,2,6-trimethylcyclohexyl)-3 hexanol),
2,6,6,8-tetramethyl-8-(methyloxy)tricyclo[5.3.1.0$^{1-5}$]undecane,
1,5,7-trimethyl-13-oxabicyclo[10.1.0]trideca-4,8-diene,
([(ethyloxy)methyl]oxy} cyclododecane,
2,4-dimethyl-2-(1,1,4,4-tetramethyltetralin-6-yl)-1,3-dioxolane, and wherein said at least one fragrance material having a fruity note is selected from the group consisting of:
di-isobutyl carbinyl acetate
allyl cyclohexyl propionate
phenylethyl isoamyl ether
(2E)-1-(2,2,6-trimethylcydohex-3-en-1-yl)but-2-en-1-one
dimethyl benzyl carbinyl acetate
ethyl 2,6,6-trimethylcyclohexa-1,3-diene-1-carboxylate
2,6-tricyclo[5.2.1.0$^{26}$]dec-4-en-8-yl propanoate 5-decalactone
δ-decalactone
γ-decalactone
2-(1,1-dimethylethyl)cyclohexyl acetate y-dodecalactone
y-dodecalactone
[8]δ-dodecalactone
γ-undecalactone
[8]δ-undecalactone
ethyl tricyclo[5.2.1.0$^{2.6}$]decane-2-carboxylate
2-methyldecanenitrile
tricyclo[5.2.1.0$^{2.6}$]dec-4-en-8-yl isobutyrate
tricyclo[5.2.1.0$^{2.6}$]dec-4-en-8-yl acetate
2-Ethyl-N-methyl-N-(3-methyl phenyl)butanamide
2-hexylcyclopentanone
2,4,4,7-trimethyl-6,8-nonadienone oxime
2-[2-(4-methylcyclohex-3-en-1-yl)propyl]cyclopentanone 2,7-dimethyl-10-(1-methylethyl)-1-oxaspiro[4.5]deca-3,6-diene tricyclo[5.2.1.0$^{2,6}$]dec-3-en-8-yl 2,2-dimethylpropanoate, wherein the weight ratio of amber material to fruity material is within the range of 1:10 to 3:1 and total amount of material having an amber note and material having a fruity note is at least 30% by weight.

2. A perfume composition according to claim 1, wherein the total amount of material having an amber note and material having a fruity note is at least 50% by weight and no group A amber material is present.

3. A perfume composition, comprising at least 1.0% by weight of one or more materials having a fruity note; and at least 0.5% by weight of at least one material having an amber note selected from at least one of group A and group B below, wherein the total amount of material having an amber note and material having a fruity note in the composition
   (a) is at least about 3% by weight if no amber material from group B is present,
   (b) at least about 25% by weight if no amber material from group A is present, or
   (c) where materials from both groups A and B are each present in an amount of at least 0.1% w/w, the total amount of amber and fruity materials together is at least 3% by weight where the total weight percentage of group A materials, $W_A$, is equal to or greater than 0.5% or the total amount of amber and fruity materials together is at least $3+22'(0.5-W_A)$ % by weight where $W_A$ is less than 0.5%
   wherein group A comprises materials with an amber note having an odour threshold lower than that of 1-(2,3,8,8-tetramethyl-1,2,3,4,5,6,7,8-octahydronaphthalen-2-yl)ethanone and group B comprises materials with an amber note having an odour threshold equal to or higher than that of 1-(2,3,8,8-tetramethyi-1,2,3,4,5,6,7,8-octahydronaphthalen-2-yl)ethanone; provided also that the weight ratio of material having an amber note to material having a fruity note in the composition is in the range about 1:30 to 30:1,
   and wherein said at least one fragrance material having an amber note is selected from the group consisting of:
   1-(2,3,8,8-tetramethyl-1,2,3,4,5,6,7,8-octahydronaphthalen-2-yl)ethanone,
   2-methoxyethoxycyclododecane,
   2-(2,4-dimethylcyclohex-3-en-1-yl)-5-methyl-5-(1-methyipropyl)-1,3-dioxane,
   3a,6,6,9a-tetramethyldodecahydronaphtho[2,1-{b}]furan,
   1-[2-(1,1-dimethylethyl)cyclohexyloxy]butan-2-ol,
   5,5,8,13-tetramethyl-14,16-dioxatetracyclo [11.2.1.0$^{1,10}$.0$^{4,9}$]hexadecane,
   3a-ethyl-6,6,9a-trimethyldodecahydronaphtho[2,1-{b}] furan,
   2-(cyclododecyl)-propan-l-ol,
   methyl 2,6,10-trimethyl-2,5,9 cyclododecatriene-1-yl ketone,
   (1-(2,2,6-trimethylcyclohexyl)-3 hexanol),
   2,6,6,8-tetramethyl-8-(methyloxy)tricyclo[5.3.1.0$^{1,5}$]undecane,
   1,5,7-trimethyl-13-oxabicyclo[10.1.0]trideca-4,8-diene,
   ([(ethyloxy)methyl]oxy}cyclododecane,
   2,4-dimethyl-2-(1,1,4,4-tetramethyltetralin-6-yl)-1,3-dioxolane
   and wherein said at least one fragrance material having a fruity note is selected from the group consisting of:
   (2E)-1-(2,2,6-trimethylcyclohex-3-en-1-yl)but-2-en-1-one
   ethyl 2,6,6-trimethylcyclohexa-1,3-diene-1-carboxylate
   tricyclo[5.2.1.0$^{2,6}$]dec-4-en-8-ylpropanoate
   γ-undecalactone
   2-methyldecanenitrile
   tricyclo[5.2.1.0$^{2,6}$]dec-4-en-8-yl isobutyrate
   tricyclo[5.2.1.0$^{2,6}$]dec-4-en-8-yl acetate
   2-ethyl-N-methyl-N-(3-methylphenyl)butanamide,
   tricyclo[5.2.1.0$^{2,6}$]dec-3-en-8-yl 2,2-dimethyl propanoate
   2-[2-(4-methylcyclohex-3-en-1-yl)propyl]cyclopentanone
   2,7-dimethyl-10-(1-methylethyl)-1-oxaspiro[4.5]deca-3,6-diene and
   tricyclo[5.2.1.0$^{2,6}$]dec-3-en-8-yl 2,2-dimethylpropanoate,
   said composition comprising at least two materials having a fruity note and comprising at least 8% by weight of one or more materials having an amber note, and at least 10% by weight of at least two materials having a fruity note.

* * * * *